United States Patent [19]

Kluge et al.

[11] 4,302,469
[45] Nov. 24, 1981

[54] 2-(1,4-BENZODIOXAN-2-YLALKYL-)IMIDAZOLES USEFUL AS ANTIDEPRESSANTS

[75] Inventors: Arthur F. Kluge, Los Altos; Arthur M. Strosberg, Portola Valley, both of Calif.; Roger Whiting; George Christie, both of Edinburgh, Scotland

[73] Assignee: Syntex (U.S.A.) Inc., Palo Alto, Calif.

[21] Appl. No.: 185,832

[22] Filed: Sep. 10, 1980

[51] Int. Cl.³ ................ C07D 407/06; A61K 31/415
[52] U.S. Cl. ............................... 424/273 R; 548/336
[58] Field of Search ............. 548/336; 424/273 R

[56] References Cited

U.S. PATENT DOCUMENTS

| | | | |
|---|---|---|---|
| 2,979,511 | 4/1961 | Krapcho et al. | 260/309.6 |
| 3,360,529 | 12/1967 | Smith-Kline | 260/340.3 |
| 3,829,411 | 8/1974 | Smith-Kline | 260/158 |
| 3,944,549 | 3/1976 | Lafon | 544/295 |
| 3,959,283 | 5/1976 | Lafon | 424/250 |

FOREIGN PATENT DOCUMENTS

| | | |
|---|---|---|
| 643853 | 8/1964 | Belgium . |
| 837386 | 5/1976 | Belgium . |
| 731147 | 3/1966 | Canada . |
| 54-103893 | 8/1979 | Japan . |
| 55-015455 | 2/1980 | Japan . |
| 55-015456 | 2/1980 | Japan . |
| 730718 | 12/1973 | Netherlands . |
| 641622 | 7/1964 | South Africa . |
| 1051143 | 12/1966 | United Kingdom . |
| 1094982 | 12/1967 | United Kingdom . |

*Primary Examiner*—John M. Ford
*Assistant Examiner*—Robert C. Whittenbaugh
*Attorney, Agent, or Firm*—Kate H. Murashige; Alan M. Krubiner; Tom M. Moran

[57] ABSTRACT

2-(1,4-Benzodioxan-2-ylalkyl)imidazoles having the general formula:

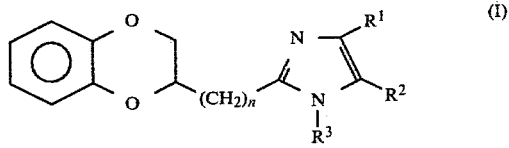

wherein $R^1$, and $R^2$ and $R^3$ are independently selected from the group consisting of hydrogen, and alkyl, and wherein n is an integer equal to 0, 1 or 2, and the pharmaceutically acceptable acid addition salts thereof, are useful as antidepressants.

16 Claims, No Drawings

2-(1,4-BENZODIOXAN-2-YLALKYL)IMIDAZOLES USEFUL AS ANTIDEPRESSANTS

BACKGROUND OF THE INVENTION

1. Field of the Invention

The present invention is concerned with compounds, compositions and methods useful for reducing, inhibiting, or preventing depression in human beings. In particular, compounds of benzodioxane substituted in the 2-position with substituents containing imidazole are thus useful.

2. Prior Art

A large number of compounds, in which the 1,4-benzodioxane system is substituted at the 2-position by a side chain containing nitrogen have been prepared, and shown to be active either in the central nervous system and/or the cardiovascular system. There appears to be no standard assay system for discriminating among the various types of effects of compounds on these target tissues; therefore the prior art is often non-specific as to the exact mode of action of the compounds tested. However, a variety of compounds having the general formula

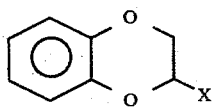

where X contains nitrogen in fairly close proximity to the ring are physiologically active. None is entirely satisfactory as an antidepressant. Those preparations closest in structure to the present invention are described in South African Pat. No. 64/622, Canadian Pat. No. 731,147, Belgian Pat. Nos. 643,853 and 837,386, U.S. Pat. Nos. 2,979,511, 3,360,529, 3,829,441, 3,944,549 and 3,959,283 British Pat. Nos. 1,051,143 and 1,094,982, Japanese Pat. Nos. 54/103,893, 55/015,456 and 55/015,455, and Dutch Pat. No. 730,718.

SUMMARY OF THE INVENTION

Imidazole derivatives of the 1,4-benzodioxan-2-yl system having the general formula

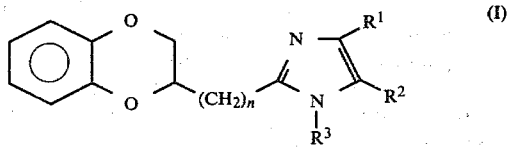

wherein $R^1$, $R^2$ and $R^3$ are independently selected from the group consisting of hydrogen and alkyl and n is an integer equal to 0, 1 or 2; and the pharmaceutically acceptable acid addition salts thereof, are novel.

Therefore, the present invention relates to compounds in the class described above, to the methods of preparation thereof, to pharmaceutical compositions containing such compounds, and to methods pertaining to their use.

DETAILED DESCRIPTION OF THE INVENTION

As used herein:

"alkyl" means a branched or unbranched saturated hydrocarbon chain containing 1–6 carbon atoms, such as methyl, ethyl, propyl, tert-butyl, n-hexyl and the like;

"pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

A set of preferred embodiments of the present invention is that wherein n=1, and $R^1$, $R^2$ and $R^3$ are each independently selected from the group consisting of hydrogen, ethyl, isopropyl, n-propyl, and n-butyl.

Another preferred embodiment of the present invention is that wherein $R^3$ is methyl, $R^1$ and $R^2$ are hydrogen and n=1, i.e. 1-methyl-2-(1,4-benzodioxan-2-ylmethyl)imidazole; and the pharmaceutically acceptable acid addition salts thereof.

Another set of preferred embodiments are those wherein $R^1$, $R^2$ and $R^3$ are hydrogen and n=0, 1 or 2, i.e.:
2-(1,4-benzodioxan-2-yl)imidazole;
2-(1,4-benzodioxan-2-ylmethyl)imidazole; or
[2-(1,4-dibenzodioxan-2-yl)ethyl]imidazole
and the pharmaceutically acceptable acid addition salts thereof.

An especially preferred embodiment is that wherein $R^1$ and $R^2$ are hydrogen, $R^3$ is ethyl, and n=1, i.e. 1-ethyl-2-(1,4-benzodioxan-2-ylmethyl)imidazole.

Compounds of Formula I are prepared by the reaction sequence:

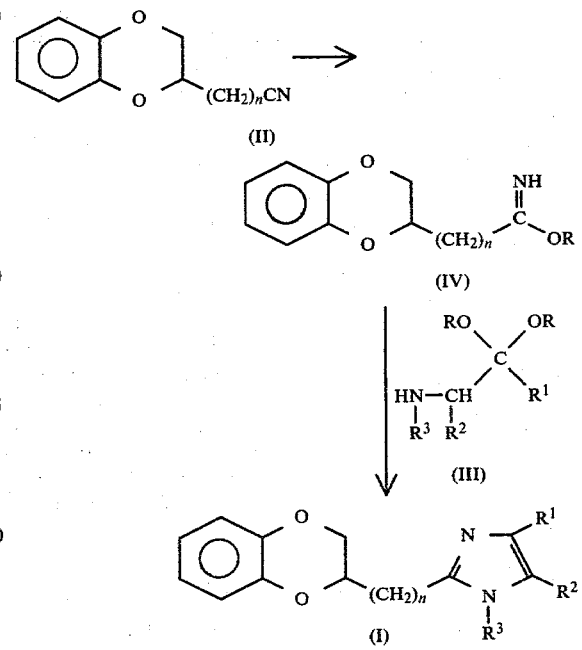

wherein each R in (III) and (IV) is independently alkyl and the two R groups in (III) may or may not be cyclized.

The method for preparation of (II) is described by Augstein, et al. in *J. Med. Chem.* 8,446 (1965), and of III by Adachi and Sato in *J. Org. Chem.* 37, 221 (1972).

It is to be understood that isolation and purification of the compounds and intermediates described herein, whether in the body of the specification, or Examples, can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the Examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

All of the compounds of Formula I possess at least one chiral center, i.e., the number 2 carbon of the dioxane ring at which substitution is made. Accordingly, the compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the compounds herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-$\pi$-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula (I).

In typical preparations, Compound(s) (II) is converted to (IV) by treatment with an excess of an alcohol under acidic conditions at low temperature, in the range of $-10°$ C. to $10°$ C., and in the absence or presence of an aprotic organic solvent, such as, for example diethyl ether or tetrahydrofuran. A preferred temperature range is $1°$ C.$-5°$ C.; preferred alcohols are methanol, ethanol and i-propanol; a preferred solvent is diethyl ether, and a preferred acid is anhydrous HCl.

The reaction mixture is allowed to stand at the aformentioned low temperature for several hours or days before being warmed to room temperature ($15°-30°$), and the crude product permitted to precipitate out.

The crude product is recovered and purified by conventional means; a particularly preferred isolation procedure is to recover the precipitated salt by filtration and purify it using thin layer chromatography. In this manner, 2-cyano-1,4-benzodioxane;
2-cyanomethyl-1,4-benzodiaxane; and
2-(2-cyanoethyl)-1,4-benzodioxane
may be converted to the corresponding imidates or the acid addition salts thereof.

In the succeeding conversion of (IV) to (I), treatment of (IV) with (III) leads to an intermediate of the general structure:

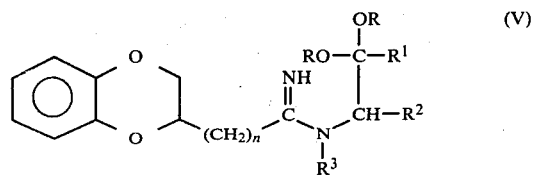

which may be isolated in crude form for conversion by treatment with acid to (I).

To effect this conversion approximately equimolar amounts of (IV) and (III) are dissolved in a polar organic solvent, such as methanol, ethanol, acetone, and the like, preferably ethanol. Reaction occurs at elevated temperatures $60°-100°$, preferably at the reflux temperature of the solvent. Reaction time will vary with temperature, but may be effected within several hours. The product is recovered by conventional means, which may include solvent evaporation, filtration, removal of solvent under reduced pressure. Further purification may be effected, if desired.

Compound (V) is converted to (I) by treatment with aqueous acid. Suitable acids include hydrochloric, sulfuric, phosphoric, nitric, oxalic, acetic and the like, at concentrations in the range of 1–6 N, preferably 2–4 N. The reaction occurs at temperature of $50°-100°$; preferably $60°-70°$. The crude product precipitates from the reaction mixture and is recovered as the salt and purified by conventional means, or may be converted to the free base by treatment with usual reagents such as sodium hydroxide, sodium carbonate, calcium hydroxide, and the like.

The subject compounds of the instant invention can thus, be isolated as free bases; however, because some compounds in base form are oils or gums, it is more convenient to isolate and characterize them as acid addition salts. These salts are prepared in the usual manner, i.e., by reaction of the base compound with a suitable inorganic or organic acid, described above. Salts formed with dibasic acids, (e.g. oxalic acid) may contain one or two molecules of base per molecule of acid. If desired, the salts can be readily converted to the compounds in base form by treatment with alkali, such as potassium carbonate, sodium carbonate or sodium or potassium hydroxide.

The compounds of Formula (I) and the pharmaceutically acceptable acid addition salts thereof exhibit CNS activity, and, in particular, are antidepressants. Said compounds have been shown to be $\alpha_2$ blockers in standard laboratory tests using pithed rats as subjects. Accordingly these compounds and pharmaceutically acceptable compositions containing them are useful in prevention, reduction and inhibition of depression in humans.

Administration of the active compounds and salts described herein can be via any of the accepted modes of administration for agents which relieve depression or affect the central nervous system including oral, parenteral and otherwise systemic in the form of solid, semisolid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula (I) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of the administration and the judgment of the prescribing physician. However, an effective dosage is in the range of 0.1–10 mg/kg/day, preferably 1–5 mg/kg/day. For an average 70 kg human, this would amount to 7–700 mg per day, or preferably 70–350 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compound of Formula (I) or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such compositions is highly dependent on the specific nature thereof, as well as the activity of the compound and the needs of the subject. However, percentages of active ingredient of 0.25% to 10% are employable, (higher if the composition is a solid which will be subsequently diluted to the above percentages), preferably in the range of 1–2%.

For systemic administration via suppository, traditional binders and carriers include, e.g. polyalkalene glycols or triglycerides. Such suppositories may be formed from mixtures containing active ingredient in the range of 0.5%–10%; preferably 1–2%.

The following preparation and examples illustrate the invention but are not intended to limit its scope.

PREPARATION I

Preparation of ethyl (1,4-benzodioxan-2-yl)acetimidate hydrochloride 17.5 g (0.10 mole) 2-cyanomethyl-1,4-benzodioxane, prepared as described by Augstein, et al, *J. Med. Chem.* 8: 446 (1965), was dissolved in a mixture containing 7 g ethanol and 50 ml diethyl ether. 4.5 g (0.15 moles) of dry HCl was bubbled though the mixture, which was then capped. The mixture was allowed to stand at 5° C. for 4 days, followed by 3 days at room temperature. The crude product imidate hydrochloride (IV) precipitated out and was harvested by filtration, and washed with 100 ml ether, followed by 3×100 ml portions of methylene chloride. The solid was then purified by thin layer chromatography using 10% methanol in chloroform as a developing solvent. The product has an $R_f$ value of 0.7–0.8; starting material moves farther in this solvent system, and none was present in the crude product. The yield of product was 15.3 g, as the hydrochloride, or 59% yield.

EXAMPLE 1

Conversion of ethyl (1,4-benzodioxan-2-yl) acetimidate. HCl to 2-(1,4-benzodioxan-2-ylmethyl)imidazole. HCl The imidate hydrochloride was further reacted as follows: 5.15 g (0.02 moles) of this material and 2.93 g (0.02 moles) of aminoacetaldehyde diacetal were placed in 70 ml ethanol and the mixture was refluxed overnight. The crude intermediate (V) was harvested by filtration, the solvent was removed, and trituration with ether gave 6.7 g of a brown oil. The oil was then stored with 100 ml 3N HCl at 60°–70° for 24 hours. The crude product (I) was harvested by filtration and solvent removed. The product was then recrystallized three times from isopropanol to give 1.8 g of white crystalline hydrochloride, m.p. 221°–224° C.(d), or a 36% yield from the imidiate hydrochloride (IV).

In a similar manner, substituting other starting materials of Formula (IV) for ethyl(1,4-benzodioxan-2-yl)acetimidate, for example
ethyl (1,4-benzodioxan-2-yl)formimidate; and
ethyl 3-(1,4-benzodioxan-2-yl)propionimidate is productive of the corresponding products:
2-(1,4-benzodioxan-2-yl)imidazole; and
2-[2-(1,4-benzodioxan-2-yl)ethyl]imidazole.

Similarly, substituting other acetals or ketals of Formula (III) for aminoacetylaldehyde diethyl acetal such as those wherein $R^1$, $R^2$ and $R^3$ are the same or different and are independently selected from the group consisting of hydrogen and lower alkyl (alkyl being defined as above) for example:
N-methylaminoacetaldehyde diethyl acetal;
2-aminopropionaldehyde diethyl acetal;
3-amino-2-propanone diethyl ketal;
2-(N-methylamino)-propionaldehyde diethyl acetal;
3-(N-methylamino)-2-propanone diethyl ketal;
3-amino-2-butanone diethyl ketal;
3-(N-methylamino)-2-butanone diethyl ketal;
N-ethylamino-acetaldehyde diethyl acetal is productive of the products:
1-methyl-2-(1,4-benzodioxan-2-ylmethyl)imidazole;
5-methyl-2-(1,4-benzodioxan-2-ylmethyl)imidazole;
4-methyl-2-(1,4-benzodioxan-2-ylmethyl)imidazole;
1,5-dimethyl-2-(1,4-benzodioxan-2-ylmethyl)imidazole;
1,4-dimethyl-2-(1,4-benzodioxan-2-ylmethyl)imidazole;
4,5-dimethyl-2-(1,4-benzodioxan-2-ylmethyl)imidazole;
1,4,5-trimethyl-2-(1,4-benzodioxan-2-ylmethyl)-imidazole;
1-ethyl-2-(1,4-benzodiaxan-2-ylmethyl)imidazole.

The list herein cited is exemplary but not all-inclusive of the variations which are produced by the herein cited method.

EXAMPLE II

Conversion of 2-(1,4-benzodioxan-2-ylmethyl)-imidazole to its hydrochloride

Excess 3% hydrogen chloride in methanol is added to a solution of 1.0 g. 2-(1,4-benzodioxan-2-ylmethyl)-imidazole in 20 ml methanol. Diethyl ether is added until precipitation is complete. The product is filtered, washed with ether, air dried and recrystallized from methanol/acetone to yield 2-(1,4-benzodioxan-2-ylmethyl)imidazole hydrochloride, m.p. 221°–224° C.(d).

In a similar manner, all compounds of Formula (I) in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE III

Conversion of a salt of 2-(1,4-benzodioxan-2-ylmethyl)imidazole to free base 2-(1,4-benzodioxan-2-ylmethyl)imidazole hydrochloride (1.0 g) suspended in 50 ml of ether is stirred with excess dilute aqueous potassium carbonate solution until the salt is completely dissolved. The organic layer is then separated, washed twice with water, dried over magnesium sulfate and evaporated to yield 2-(1,4-benzodioxan-2-ylmethyl)imidazole.

In a similar manner the acid addition salts of all compounds of Formula (I) may be converted to the corresponding compounds in free base form.

EXAMPLE IV

Direct interchange of acid addition salts of 2-(1,4-benzodioxan-2-ylmethyl)imidazole 2-(1,4-benzodioxan-2-ylmethyl)imidazolium acetate (1.0 g) is dissolved in 50 ml 50% aqueous sulfuric acid, and the solution evaporated to dryness. The product is suspended in ethanol and filtered, air dried and recrystallized from methanol/acetone to yield 2-(1,4-benzodioxan-2-ylmethyl)imidazole bisulfate.

In Examples V through VIII, the active ingredient is 2-(1,4-benzodioxan-2-ylmethyl)imidazole hydrochloride. Other compounds of Formula (I) and the pharmaceutically acceptable salts thereof may be substituted therein.

EXAMPLE V

Composition for Oral Administration

| The composition contains: | % wt./wt. |
| --- | --- |
| Active ingredient | 95% |
| Lactose | 5% |

The two ingredients are milled, mixed and dispensed into capsules containing 100 mg each; one capsule would approximate a total daily dosage.

EXAMPLE VI

Composition for Oral Administration

| The composition contains: | % wt./wt. |
| --- | --- |
| Active ingredient | 56.8% |
| Magnesium stearate | 0.9% |
| Starch | 8.6% |
| Lactose | 32.9% |
| PVP (polyvinylpyrrolidine) | 0.9% |

The above ingredients are combined and granulated using methanol as solvent. The formulation is then dried and formed into tablets (containing 200 mg of active compound) with an appropriate tableting machine.

EXAMPLE VII

Parenteral Formulation (IV)

| The composition contains: | % wt./wt. |
| --- | --- |
| Active compound | 0.25 g |
| Propylene glycol | 20. g |
| Polyethylene glycol 400 | 20. g |
| Polysorbate 80 | 1. g |
| 0.9% Saline solution qs ad | 100 ml |

The active compound is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE VIII

Suppository Formulation

| The composition contains: | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

We claim:
1. A compound of the formula

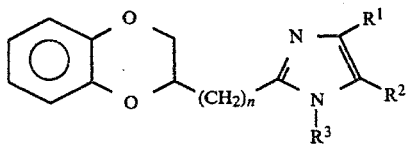

wherein $R^1$, $R^2$ and $R^3$ are independently selected from the group consisting of hydrogen and lower alkyl, and wherein n is either 0, 1, or 2, and the pharmaceutically acceptable acid addition salts thereof.

2. The compound of claim 1 wherein n=1, and $R^1$, $R^2$ and $R^3$ are each independently selected from the group consisting of hydrogen, ethyl, isopropyl, n-propyl, and n-butyl, and the pharmaceutically acceptable acid addition salts thereof.

3. The compound of claim 1 wherein n=1 and $R^1$, $R^2$ and $R^3$ are hydrogen, i.e. 2-(1,4-benzodioxan-2-ylmethyl)imidazole, and the pharmaceutically acceptable acid addition salts thereof.

4. The compound of claim 1 wherein n=0 and $R^1$, $R^2$ and $R^3$ are hydrogen, i.e., 2-(1,4-benzodioxan-2-yl)-imidazole, and the pharmaceutically acceptable acid addition salts thereof.

5. The compound of claim 1 wherein n=2 and $R^1$, $R^2$ and $R^3$ are hydrogen, i.e., 2-[(1,4-benzodioxan-2-yl)-ethyl]imidazole, and the pharmaceutically acceptable acid addition salts thereof.

6. The compound of claim 1 wherein $R^3$ is methyl, $R^1$ and $R^2$ are hydrogen and n=1, i.e. 1-methyl-2-(1,4-benzodioxan-2-ylmethyl)imidazole and the pharmaceutically acceptable acid addition salts thereof.

7. The compound of claim 1 wherein $R^3$ is ethyl, $R^1$ and $R^2$ are hydrogen and n=1, i.e. 1-ethyl-2-(1,4-benzodioxan-2-ylmethyl)imidazole and the pharmaceutically acceptable acid addition salts thereof.

8. A composition for treating depression in humans comprising a pharmaceutically acceptable non-toxic excipient and a therapeutically effective amount of a compound of the formula

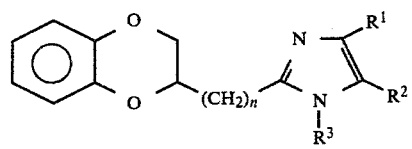

wherein $R^1$, $R^2$ and $R^3$ are independently selected from the group consisting of hydrogen and lower alkyl, and wherein n is either 0, 1, or 2, or a pharmaceutically acceptable salt thereof.

9. The composition of claim 8 wherein n=1, and $R^1$, $R^2$ and $R^3$ are each independently selected from the group consisting of hydrogen, ethyl, isopropyl, n-propyl, and n-butyl.

10. The composition of claim 8 wherein the compound of formula (I) is 2-(1,4-benzodioxan-2-yl-methyl)imidazole, or a pharmaceutically acceptable salt thereof.

11. The composition of claim 8 wherein the compound of formula (I) is 2-(1,4-benzodioxan-2-yl)-imidazole, or a pharmaceutically acceptable salt thereof.

12. The composition of claim 8 wherein the compound of formula (I) is 2-[2-(1,4-benzodioxan-2-yl)e- thyl]imidazole, or a pharmaceutically acceptable salt thereof.

13. The composition of claim 8 wherein the compound of formula (I) is 1-methyl-2-(1,4-benzodioxan-2-ylmethyl)imidazole or a pharmaceutically acceptable acid addition salt thereof.

14. The composition of claim 8 wherein the compound of formula (I) is 1-ethyl-2-(1,4-benzodioxan-2-ylmethyl)imidazole or a pharmaceutically acceptable acid addition salt thereof.

15. A method of treating depression in humans which comprises administering to a subject in need of such treatment, a therapeutically effective amount of a compound of the formula:

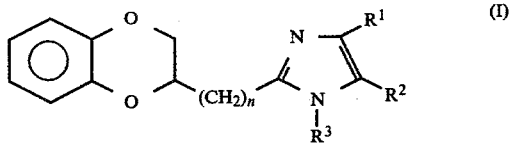

wherein $R^1$, $R^2$ and $R^3$ are independently selected from the group consisting of hydrogen and lower alkyl, and wherein n is either 0, 1, or 2, or a pharmaceutically acceptable salt thereof, or a pharmaceutical composition containing an effective amount of said compound or a pharmaceutically acceptable salt thereof.

16. A process for the production of a compound of the formula:

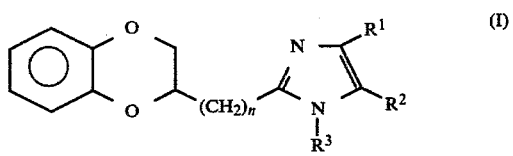

wherein $R^1$, $R^2$ and $R^3$ are independently selected from the group consisting of hydrogen and lower alkyl, and wherein n is either 0, 1, or 2, and the pharmaceutically acceptable acid addition salts thereof which comprises one or more of the following steps (a) converting an imidate of the general formula

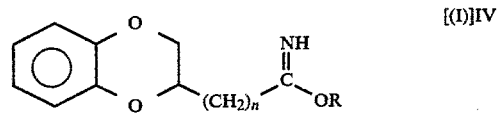

wherein R is alkyl and n is 0, 1 or 2 to the corresponding compound of formula I by treatment with a compound of the formula

wherein R, $R^1$, $R^2$ and $R^3$ are as herein defined, followed by treatment with acid; and optionally (b) converting the pharmaceutically acceptable acid addition salt to the free base; or (c) converting the free base to the pharmaceutically acceptable acid addition salt; or (d) converting a salt of the subject compound to another salt by a salt interchange.

* * * * *